(12) United States Patent  
Matoba

(10) Patent No.: US 8,422,630 B2
(45) Date of Patent: Apr. 16, 2013

(54) X-RAY INSPECTION DEVICE AND X-RAY INSPECTION METHOD

(75) Inventor: Yoshiki Matoba, Chiba (JP)

(73) Assignee: SII NanoTechnology Inc. (JP)

( * ) Notice: Subject to any disclaimer, the term of this patent is extended or adjusted under 35 U.S.C. 154(b) by 161 days.

(21) Appl. No.: 12/802,401

(22) Filed: Jun. 7, 2010

(65) Prior Publication Data
US 2010/0316187 A1 Dec. 16, 2010

(30) Foreign Application Priority Data

Jun. 12, 2009 (JP) ................................. 2009-141491
Mar. 24, 2010 (JP) ................................. 2010-068760

(51) Int. Cl.
G01N 23/06 (2006.01)
(52) U.S. Cl.
USPC ............................................. 378/58; 378/53
(58) Field of Classification Search .................... 378/58, 378/53
See application file for complete search history.

(56) References Cited

U.S. PATENT DOCUMENTS 5,768,334 A * 6/1998 Maitrejean et al. ............. 378/53
5,783,332 A * 7/1998 Amine et al. .................. 429/221
6,418,193 B1 * 7/2002 Albagli ........................ 378/158
2003/0108155 A1 * 6/2003 Wilkins et al. ............... 378/119

FOREIGN PATENT DOCUMENTS

JP 2004239776 A * 8/2004

OTHER PUBLICATIONS

Moore, A.R., "A method of accurate thickness determination of germanium wafers suitable for transistor production", IRE Transactions on Electron Devices, vol. 4, Issue 4, (1957), pp. 309-310.*

* cited by examiner

Primary Examiner — Glen Kao
(74) Attorney, Agent, or Firm — Adam & Wilks

(57) ABSTRACT

In order to prevent misdetection and erroneous detection by clearly determining only a contrast caused by a foreign matter, there are provided an X-ray inspection method and an X-ray inspection device including: an X-ray tube (11) for irradiating a measurement sample with a characteristic X-ray having energy lower than an X-ray absorption edge of one element contained in the measurement sample and having energy higher than an X-ray absorption edge of a detection element; an X-ray detector (13) for receiving a transmission X-ray obtained when the X-ray passes through the sample; and an operation portion (15) for obtaining a contrast image from a transmission image of the transmission X-ray.

8 Claims, 4 Drawing Sheets

X-RAY INSPECTION DEVICE AND X-RAY INSPECTION METHOD

BACKGROUND OF THE INVENTION

1. Field of the Invention

The present invention relates to an X-ray inspection device and an X-ray inspection method which are capable of detecting a foreign matter formed of a particular element in a sample.

2. Description of the Related Art

In recent years, a lithium-ion secondary battery, which has a higher energy density compared with that of a nickel metal hydride battery, has been increasingly adopted as a battery for an automobile, a hybrid car, an electric vehicle, and the like. The lithium-ion secondary battery is a kind of a non-aqueous electrolyte secondary battery, which has lithium ions in an electrolyte conducting electricity and does not contain metal lithium, and has already been used widely in notebook personal computers and mobile phones.

The lithium-ion secondary battery has excellent battery characteristics. However, when a foreign matter such as Fe (iron) enters an electrode during a production process, the reliability of the battery is adversely affected, such as degradation in battery characteristics as to a heat-generation property, a longevity, and the like, which has delayed the mounting of the battery on a vehicle. For example, as illustrated in FIG. 4A, an electrode (anode) of the lithium-ion secondary battery is generally formed in such a manner that a lithium cobalt oxide film 2 or a lithium manganese oxide film 2 is formed to a thickness of about 100 μm on both surfaces of an Al film 1 having a thickness of 20 μm. As illustrated in FIG. 4B, a foreign matter X such as Fe (iron) or SUS (stainless steel) may be mixed into the electrode, and if the size of the foreign matter X is tens of pm or larger, short-circuit occurs, which may cause burning of the battery and decrease in performance. Therefore, there is a demand in the lithium-ion secondary battery that a battery with the foreign matter X mixed therein be detected swiftly during production and be removed in advance.

In general, as a method of detecting a foreign matter or the like in a sample, a method using an X-ray image is known. Using this procedure, a method of detecting a foreign matter formed of a carboneous material, in which the presence/absence of the contamination of a foreign matter in a carbon-based material or the like used as a cathode of a lithium-ion secondary battery is detected based on an X-ray image, has been proposed conventionally (see Japanese Patent Application Laid-open No. 2004-239776 (claims)).

The above-mentioned related art has the following problem.

Specifically, with the conventional method of detecting a foreign matter, the presence/absence of a foreign matter is merely detected based on the intensity of an X-ray image. Therefore, if the atomic number of a foreign matter is largely different from that of a sample, a clear contrast is obtained. However, if the atomic number of the foreign matter is close to that of the sample, a contrast is not clear, which makes discrimination therebetween more difficult. For example, there is no clear contrast between Co (atomic number: 27) contained as one of constituent elements in an electrode (positive plate) to be a measurement sample and Fe (atomic number: 26) that is an element constituting a foreign matter to be detected. Therefore, with the conventional method of detecting a foreign matter, it is impossible to determine whether a contrast is caused by a portion 2a where a constituent material is partially thick as illustrated in FIG. 4A or caused by the foreign matter X as illustrated in FIG. 4B in an X-ray image T of an electrode (positive plate) that is a measurement sample S, which may lead to misdetection or erroneous detection.

SUMMARY OF THE INVENTION

The present invention has been made in view of the above-mentioned problem, and therefore has an object to provide an X-ray inspection device and an X-ray inspection method which are capable of preventing misdetection and erroneous detection by clearly determining only a contrast caused by a foreign matter.

The present invention adopts the following configurations so as to solve the above-mentioned problem. Specifically, in the X-ray inspection device and the X-ray inspection method according to the present invention, a measurement sample is irradiated with a characteristic X-ray having energy lower than an X-ray absorption edge of one element contained in the measurement sample and having energy higher than an X-ray absorption edge of an element to be detected (hereinafter, referred to as "detection element"); an X-ray detector receives a transmission x-ray obtained when the characteristic x-ray passes through the measurement sample and detects an intensity of the transmission X-ray; and a contrast image is obtained through operation based on a transmission image showing a distribution of the detected intensity of the transmission X-ray.

Further, in order to obtain the characteristic X-ray for the irradiation on the measurement sample, there is used a filter formed of an element having an X-ray absorption edge of energy between a Kα-ray and a Kβ-ray of the characteristic X-ray for removing the Kβ-ray from the characteristic X-ray.

In the X-ray inspection device and the X-ray inspection method, a transmission image is obtained by irradiating the sample with the monochromatized characteristic X-ray having energy lower than the X-ray absorption edge of one element contained in the measurement sample and having energy higher than the X-ray absorption edge of the detection element. Therefore, a clear contrast image may be obtained regarding a particular element. More specifically, by using a monochromatic X-ray having the higher energy than the X-ray absorption edge of the above-mentioned element instead of an X-ray in which various energies are mixed, such as a white X-ray, a clear contrast image of an element to be measured can be obtained irrespective of the presence of another element whose atomic number is close to that of the element to be measured.

Further, the filter formed of the element having the X-ray absorption edge of energy between the Kα-ray and the Kβ-ray of the characteristic X-ray is placed between the measurement sample and the X-ray tube, and hence the Kβ-ray of the characteristic X-ray emitted from the X-ray tube can be cut with the filter. Thus, only a desired characteristic X-ray is extracted to irradiate the sample, and hence the contrast of the element to be measured becomes clearer.

Further, in the X-ray inspection device, the measurement sample contains lithium cobalt oxide, the X-ray tube includes a Ni target tube, the detection element includes Fe, and the filter includes Co foil.

More specifically, in the X-ray inspection device of the present invention, when a measurement sample typically containing lithium cobalt oxide is used as a measurement sample, and a foreign matter mainly containing Fe is detected in the measurement sample, a characteristic X-ray (7.477 keV) emitted from a Ni target tube is used as a characteristic X-ray having energy lower than an X-ray absorption edge (7.709 keV) of Co that is one constituent element of lithium cobalt oxide and having energy higher than an X-ray absorption edge (7.111 keV) of Fe that is a detection element. This enables Fe to be detected with a clear contrast image, using an inexpensive X-ray tube.

Further, the X-ray inspection device is capable of extracting only a Ni—Kα characteristic X-ray (7.477 keV), using a filter of Co (X-ray absorption edge=7.709 keV) foil, and irradiating the measurement sample with the Ni—Kα characteristic X-ray.

Further, in the X-ray inspection device, the measurement sample contains lithium manganese oxide, the X-ray tube includes an Fe target tube, the detection element includes Cr, and the filter includes Mn foil.

More specifically, in the X-ray inspection device of the present invention, when a measurement sample typically containing lithium manganese oxide is used as a measurement sample, and a foreign matter mainly containing Cr is detected in the measurement sample, a characteristic X-ray (6.403 keV) emitted from an Fe target tube is used as a characteristic X-ray having energy lower than an X-ray absorption edge (6.540 keV) of Mn that is one constituent element of lithium manganese oxide and having energy higher than an x-ray absorption edge (5.989 keV) of Cr that is a detection element. This enables Cr to be detected with a clear contrast image, using an inexpensive X-ray tube.

Further, the X-ray inspection device is capable of extracting only an Fe—Kα characteristic X-ray (6.403 keV), using a filter of Mn (X-ray absorption edge=6.540 keV) foil, and irradiating the measurement sample with the Fe—Kα characteristic X-ray.

The present invention exhibits the following effects.

According to the X-ray inspection device and the X-ray inspection method of the present invention, a contrast image is obtained from a transmission image obtained by irradiating a sample with a characteristic X-ray having energy lower than an X-ray absorption edge of one element contained in a measurement sample and having energy higher than an X-ray absorption edge of a detection element. Therefore, a clear contrast image may be obtained regarding a particular element to be detected. Further, the filter formed of an element having an X-ray absorption edge of energy between the Kα-ray and the Kβ-ray of the characteristic X-ray emitted from the X-ray tube is placed between the sample and the X-ray tube. Therefore, only a desired characteristic X-ray (Kα-ray) may be extracted to irradiate the sample, and hence a contrast of the detection element to be measured may be obtained clearly irrespective of the presence of an element whose atomic number is close to that of the sample.

Accordingly, using the X-ray inspection device and the X-ray inspection method, for example, a foreign matter of a particular element in a lithium-ion secondary battery or the like can be detected swiftly with high precision.

DETAILED DESCRIPTION OF THE PREFERRED EMBODIMENTS

Hereinafter, one embodiment of an X-ray inspection device and an X-ray inspection method according to the present invention is described with reference to FIGS. 1 to 3B.

Figure 1:
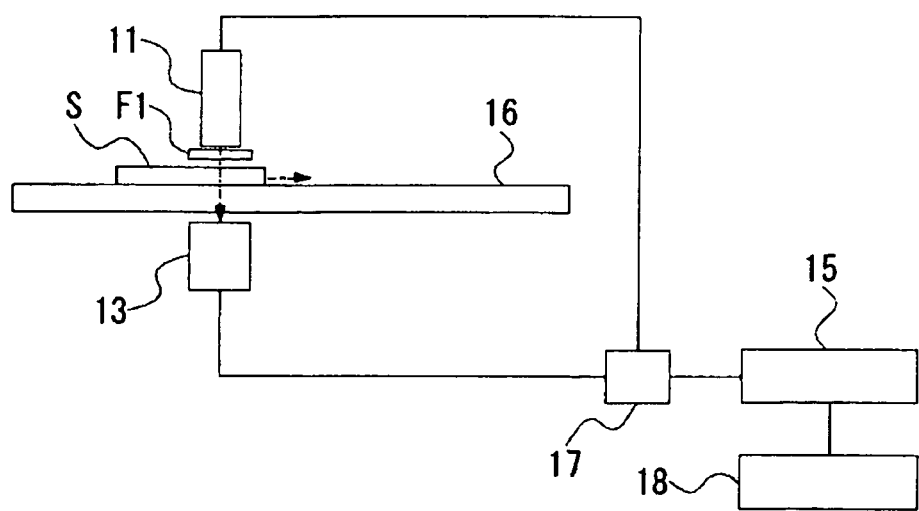
FIG. 1 is an overall schematic structural view illustrating one embodiment of an X-ray inspection device and an X-ray inspection method according to the present invention.

As illustrated in FIG. 1, the X-ray inspection device includes: an X-ray tube 11 for irradiating a measurement sample S with an X-ray having energy lower than an X-ray absorption edge of one element contained in the measurement sample S and having energy higher than an X-ray absorption edge of a detection element; an X-ray detector 13 for receiving a transmission X-ray obtained when the X-ray passes through the measurement sample S and detecting an intensity of the transmission X-ray; and a display portion 18 for displaying a transmission image showing a distribution of the detected intensity of the transmission X-ray.

Further, the X-ray inspection device includes a belt conveyer 16 that is a sample stage capable of moving horizontally with the measurement sample S placed thereon, a control portion 17 connected to and controlling each of the above-mentioned components.

Further, in the X-ray inspection device, a filter F1 formed of an element having an X-ray absorption edge of energy between a Kα-ray and a Kβ-ray of a characteristic X-ray emitted from an X-ray tube is placed between the measurement sample S and the X-ray tube 11.

The measurement sample S is, for example, an electrode or the like used in a lithium-ion secondary battery, and the detection element is, for example, Fe or Cr in SUS that may be mixed in the electrode as a foreign matter.

Assuming that the detection element is Fe, a Ni tube having a Ni target is adopted as the X-ray tube 11. The X-ray tube 11 formed of the Ni tube emits a Ni—Kα characteristic X-ray (7.477 keV) as an X-ray having energy higher than a K-absorption edge (7.111 keV) of Fe, for example.

Further, at this time, Co foil is adopted as the filter F1.

Assuming that the detection element is Cr, an Fe tube having an Fe target is adopted as the X-ray tube 11.

The X-ray tube 11 formed of the Fe tube emits an Fe-Kα characteristic X-ray (6.403 keV) as an X-ray having energy higher than a K-absorption edge (5.988 keV) of Cr, for example.

Further, at this time, Mn foil is adopted as the filter F1.

Table 1 shows energy of a characteristic X-ray that may be adopted as an X-ray and energy of an X-ray absorption edge of an element that may be adopted as the filter F1 as examples in the case where the detection element is Fe or Cr.

TABLE 1

|  |  | Energy (keV) |
|---|---|---|
| Case where Fe is paid attention to | Fe absorption edge | 7.111 |
|  | Ni—Kα characteristic X-ray | 7.477 |
|  | Ni—Kβ characteristic X-ray <Filter> | 8.264 |
|  | Co absorption edge | 7.709 |
| Case where Cr is paid attention to | Cr absorption edge | 5.988 |
|  | Fe—Kα characteristic X-ray | 6.403 |
|  | Fe—Kβ characteristic X-ray <Filter> | 7.057 |
|  | Mn absorption edge | 6.537 |

The X-ray tubes emit an X-ray generated when thermions generated from a filament (anode) in the tube are accelerated by a voltage applied between the filament (anode) and a target (cathode) to collide against the target, as a primary X-ray from a window of beryllium foil or the like.

The X-ray detector 13 is an X-ray line sensor placed below the belt conveyer 16 so as to be opposed to the corresponding X-ray tube 11. As the X-ray line sensor, a scintillator system in which an X-ray is converted into fluorescent light by a fluorescent plate and converted into a current signal by light-receiving elements aligned in a row, a semiconductor system in which a plurality of semiconductor detecting elements are aligned in a row, or the like is adopted. Further, the X-ray sensor may be an X-ray area sensor in which light-receiving elements are arranged two-dimensionally, instead of the one-row line.

The control portion 17 is a computer configured by a CPU or the like.

Further, the operation portion 15 is an operation processing circuit or the like, which creates a transmission image by image processing based on a signal from the X-ray detector 13 input via the control portion 17 and displays the image on the display portion 18. The processing circuit of the operation portion 15 may be integrally provided in and the control portion 17. Further, the display portion 18 is capable of displaying various kinds of information in accordance with the control from the control portion 17.

Next, the X-ray inspection method using the X-ray inspection device of this embodiment is described with reference to FIGS. 1 to 3B. In the X-ray inspection method, for example, the measurement sample S is a lithium cobalt oxide electrode, the foreign matter X contained in the measurement sample S is iron, the detection element is Fe, and a Ni tube is adopted as the X-ray tube 11.

First, the measurement sample S is moved to a position opposed to the X-ray tube 11 by the belt conveyer 16.

Then, the measurement sample S is irradiated with a Ni—Kα characteristic X-ray as an X-ray from the X-ray tube 11 formed of the Ni tube, and a transmission X-ray passing through the measurement sample S is detected by the X-ray detector 13. At this time, while being moved by the belt conveyer 16, the measurement sample S is scanned as a whole, and an entire intensity distribution of the transmission X-ray is obtained.

At this time, the X-ray (Ni—Kα characteristic X-ray=7.477 keV) emitted from the X-ray tube 11 formed of the Ni tube has energy lower than an X-ray absorption edge (7.709 keV) of Co that is one of the constituent elements of a lithium cobalt oxide battery that is the measurement sample S and energy higher than an X-ray absorption edge (7.112 keV) of the detection element Fe. Thus, the X-ray passes through the lithium cobalt oxide that is the measurement sample S and is absorbed by iron that is the foreign matter X, and thus a high contrast image is obtained. Further, before irradiating the measurement sample S, a characteristic X-ray (Ni—Kβ characteristic X-ray (8.264 keV), etc.) having energy higher than the X-ray absorption edge of Co and an X-ray of background are cut by being absorbed by the filter F1 formed of the Co foil, and substantially only the Ni—Kα characteristic X-ray (7.477 keV) irradiates the measurement sample S.

Here, as the "one element contained in the measurement sample", an element that may be representative of the measurement sample is selected so that "an X-ray having energy lower than an X-ray absorption edge of one element contained in a measurement sample and having energy higher than an X-ray absorption edge of a detection element irradiates the measurement sample" according to the present invention. Thus, in the case of this example, Co that is one of the constituent elements of the lithium cobalt oxide battery is selected based on the relationship between the detection element and the X-ray.

The intensity distribution of the transmission X-ray thus obtained is subjected to image processing by the operation portion 15 to create a transmission image.

Figure 2:
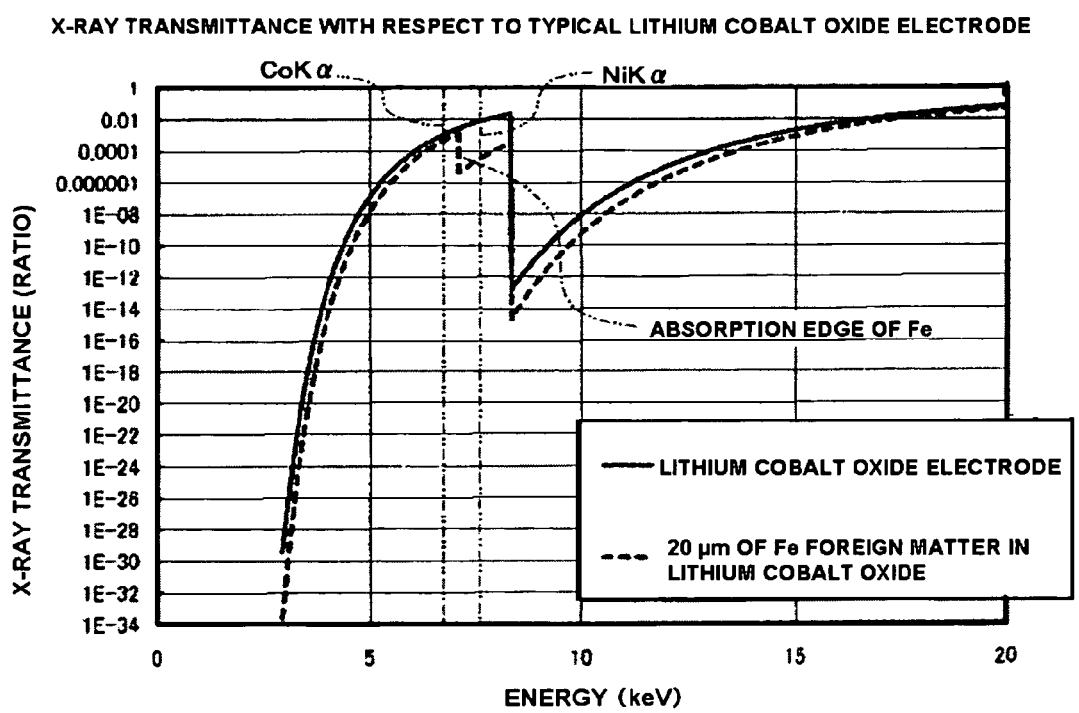
FIG. 2 is a diagram illustrating a relationship between X-ray energy and X-ray transmittance according to the embodiment of the present invention.

The X-ray transmittance with respect to the lithium cobalt oxide electrode decreases at energy corresponding to the X-ray absorption edge of Fe, as illustrated in FIG. 2, for example, in the case where a foreign matter of Fe of 20 μm is contained, compared with the case where no foreign matter is contained. Further, the Ni—Kα characteristic X-ray that is an X-ray has energy corresponding to the higher energy side of the X-ray absorption edge of Fe.

Figure 3A:
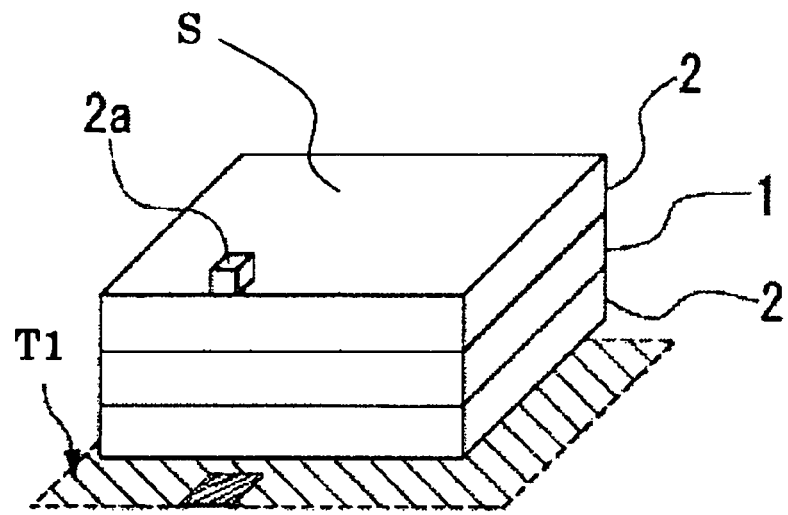
FIG. 3A is an explanatory diagram illustrating an X-ray image in the case of including a portion where the thickness is partially different during X-ray transmission according to the embodiment of the present invention.
Figure 3B:
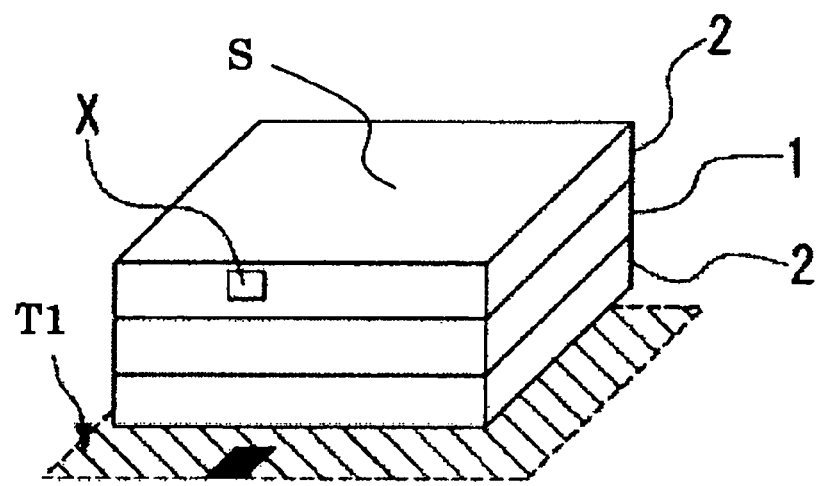
FIG. 3B is an explanatory diagram illustrating an X-ray image in the case of including a foreign matter in a surface layer during X-ray transmission according to the embodiment of the present invention.
Figure 4A:
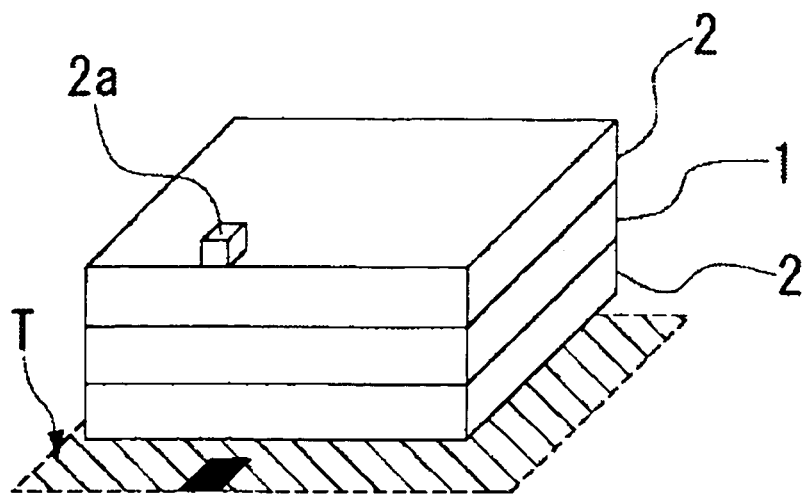
FIG. 4A is an explanatory diagram illustrating an X-ray image in the case of including a portion where the thickness is partially different during X-ray transmission according to a conventional example.
Figure 4B:
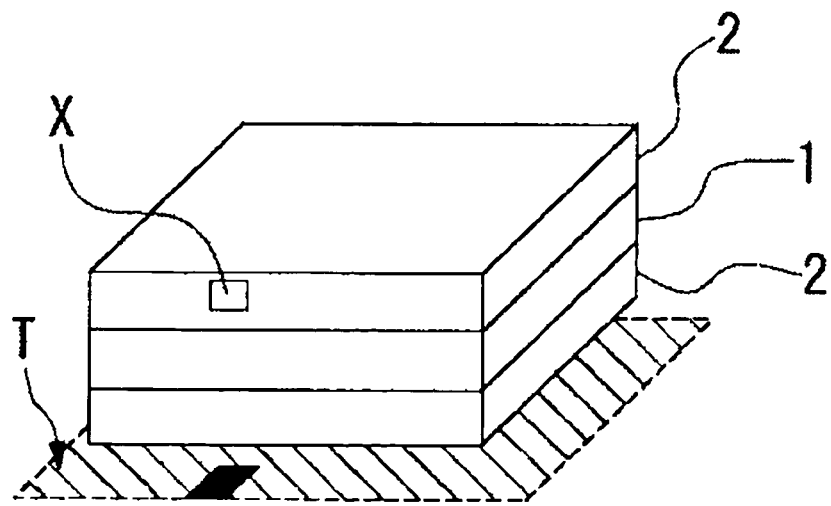
FIG. 4B is an explanatory diagram illustrating an X-ray image in the case of including a foreign matter in a surface layer during X-ray transmission according to the conventional example.

Therefore, as illustrated in FIG. 3A, in the case where there is a partially thick portion 2a in a constituent material (electrode material in which the lithium cobalt oxide films 2 are laminated on both surfaces of the Al film 1) of the measurement sample S, a clear contrast does not appear in a portion corresponding to the partially thick portion 2a in a transmission image T1 created by the X-ray tube 11 formed of the Ni tube. As illustrated in FIG. 3B, in the case where there is the foreign matter X of Fe in the measurement sample S, a clear contrast is shown in a portion corresponding to the foreign matter X in the transmission image T1 created by the X-ray tube 11 formed of the Ni tube. More specifically, the X-ray transmittance of the Ni—Kα characteristic X-ray having energy higher than the X-ray absorption edge of Fe is lower with respect to the foreign matter X of Fe. Therefore, the amount of the Ni—Kα characteristic X-ray passing through the portion of the foreign matter X becomes smaller than the amount passing through other portions, and the portion of the foreign matter X becomes a dark portion, which causes a contrast.

The X-ray inspection method of detecting the foreign matter X in a lithium cobalt oxide electrode has been described. However, the present invention is similarly applicable to the inspection of a foreign matter in lithium manganese oxide used in a positive plate and the inspection of a foreign mater in a laminated material between Al (aluminum) and C (graphite) used in a negative plate, as an electrode material used in a lithium-ion secondary battery.

Regarding the X-ray transmittances to those materials, in the case where there is the foreign matter X of Fe, an X-ray transmittance decreases at the X-ray absorption edge of Fe. Thus, even in the case of detecting the foreign matter X in those materials, a contrast image with a portion of the foreign matter X emphasized can be obtained by using an X-ray (for example, a Ni—Kα characteristic X-ray from a Ni tube) having energy lower than that of an X-ray absorption edge of a main element constituting the material and having energy higher than the X-ray absorption edge of Fe.

Thus, with the X-ray inspection device and the X-ray inspection method of this embodiment, a contrast image is obtained from the transmission image T1 obtained by irradiating the measurement sample S with an X-ray having energy lower than the X-ray absorption edge of one element contained in the measurement sample and having energy higher than the X-ray absorption edge of the detection element. Therefore, a clear contrast image may be obtained regarding a particular detection element. More specifically, by irradiating a characteristic X-ray that passes through the measurement sample, has an X-ray absorption edge on a higher energy side of the X-ray absorption edge of the above-mentioned detection element, and causes a difference in transmission X-ray detection amount, instead of an X-ray in which various energies are mixed, such as a white X-ray, a clear contrast image of an element to be measured may be obtained even in the presence of another element whose atomic number is close to that of the element to be measured.

Further, the filter F1 formed of an element having an X-ray absorption edge of energy between a Kα-ray and a Kβ-ray of a characteristic X-ray emitted from the X-ray tube is placed between the measurement sample S and the X-ray tube 11. Therefore, unnecessary radiation (not only the characteristic X-ray from the X-ray tube 11, but also a characteristic X-ray having energy higher than that of the characteristic X-ray from the X-ray tube 11 and an X-ray in background) may be cut with the filter F1. Thus, only a desired characteristic X-ray is extracted to irradiate the measurement sample S, and hence the contrast of the element to be measured becomes clearer.

Further, in the case where the measurement sample contains lithium cobalt oxide, assuming that Fe is the detection element, the foreign matter X of Fe can be detected with a clear contrast image by an inexpensive X-ray tube, using the X-ray tube 11 formed of a Ni tube capable of emitting a characteristic X-ray of Ni located on the higher energy side of the X-ray absorption edge of Fe.

Further, the filter is Co foil, and hence only the Ni—Kα characteristic X-ray (7.477 keV) can be extracted with the X-ray absorption edge (7.709 keV) of Co. More specifically, the Ni—Kβ characteristic X-ray (8.264 keV) is cut with the X-ray absorption edge (7.709 keV) of Co.

Further, in the case where the measurement sample contains lithium cobalt oxide, assuming that Cr is the detection element, the foreign matter X of SUS or the like containing Cr can be detected with a clear contrast image by an inexpensive X-ray tube, using the X-ray tube 11 formed of an Fe tube capable of emitting a characteristic X-ray of Fe located on the higher energy side of the X-ray absorption edge of Cr.

Further, in the case where the X-ray tube 11 is the Fe tube, the filter is Mn foil, and hence only the Fe—Kα characteristic X-ray (6.403 keV) can be extracted with the X-ray absorption edge (6.537 keV) of Mn. More specifically, the Fe—Kβ characteristic X-ray (7.057 keV) is cut with the X-ray absorption edge (6.537 keV) of Mn.

It should be noted that the technical scope of the present invention is not limited to the above-mentioned embodiment, and may be variously modified as long as it does not depart from the spirit of the present invention.

What is claimed is:

1. A method for detecting whether Fe is present as foreign matter in a manufactured sample containing lithium cobalt oxide, comprising the steps:
   irradiating the manufactured sample containing lithium cobalt oxide with characteristic x-rays generated by an x-ray tube having Ni target tube, the characteristic x-rays having energy lower than an x-ray absorption edge of a constituent element of the sample and having energy higher than an x-ray absorption edge of Fe so that Fe present in the sample absorbs the characteristic x-rays to a greater degree than the constituent element of the sample;
   detecting the intensity of the characteristic x-rays that pass through the sample; and
   creating an image which shows a distribution of the detected intensity of the characteristic x-rays passing through the sample and in which Fe present in the sample appears in clear contrast.

2. A method according to claim 1; wherein the irradiating step includes, before irradiating the sample with characteristic x-rays, passing the characteristic x-rays through a Co foil filter having an x-ray absorption edge of energy higher than that of the characteristic x-rays.

3. A method according to claim 1; wherein the manufactured sample is an electrode of a secondary battery.

4. A method according to claim 1; wherein the manufactured sample is an electrode of a lithium-ion secondary battery.

5. A method for detecting whether Cr is present as foreign matter in a manufactured sample containing lithium manganese oxide, comprising the steps:
   irradiating the manufactured sample containing lithium manganese oxide with characteristic x-rays generated by an x-ray tube having an Fe target tube, the characteristic x-rays having energy lower than an x-ray absorption edge of a constituent element of the sample and having energy higher than an x-ray absorption edge of Cr so that Cr present in the sample absorbs the characteristic x-rays to a greater degree than the constituent element of the sample;
   detecting the intensity of the characteristic x-rays that pass through the sample; and
   creating an image which shows a distribution of the detected intensity of the characteristic x-rays passing through the sample and in which Cr present in the sample appears in clear contrast.

6. A method according to claim 5; wherein the irradiating step includes, before irradiating the sample with characteristic x-rays, passing the characteristic x-rays through a Mn foil filter having an x-ray absorption edge of energy higher than that of the characteristic x-rays.

7. A method according to claim 5; wherein the manufactured sample is an electrode of a secondary battery.

8. A method according to claim 5; wherein the manufactured sample is an electrode of a lithium-ion secondary battery.

* * * * *